United States Patent [19]
Griffin

[11] Patent Number: 5,562,657
[45] Date of Patent: Oct. 8, 1996

[54] SIDE FIRE LASER CATHETER METHOD AND APPARATUS

[76] Inventor: Stephen E. Griffin, 2108 E. Solano Dr., Phoenix, Ariz. 85016

[21] Appl. No.: 308,369

[22] Filed: Sep. 19, 1994

[51] Int. Cl.$^6$ ............................................. A61B 17/32
[52] U.S. Cl. ............................ 606/17; 606/15; 606/16; 606/13
[58] Field of Search ..................... 606/7, 10–17; 607/88, 89

[56] References Cited

U.S. PATENT DOCUMENTS

| | | |
|---|---|---|
| 4,541,159 | 9/1985 | Michel et al. . |
| 4,566,438 | 1/1986 | Liese et al. . |
| 4,592,353 | 6/1986 | Daikuzono ............................ 606/16 |
| 4,718,417 | 1/1988 | Kittrell et al. . |
| 4,740,047 | 4/1988 | Abe et al. . |
| 4,852,567 | 8/1989 | Sinofsky . |
| 4,862,887 | 9/1989 | Weber et al. ........................... 606/7 X |
| 4,878,725 | 11/1989 | Hessel et al. . |
| 4,917,084 | 4/1990 | Sinofsky . |
| 4,985,029 | 1/1991 | Hoshino . |
| 5,093,877 | 3/1992 | Aita et al. ............................. 606/15 X |
| 5,163,935 | 11/1992 | Black et al. ............................... 606/17 |
| 5,169,395 | 12/1992 | Narciso, Jr. . |
| 5,188,632 | 2/1993 | Goldenberg . |
| 5,193,526 | 3/1993 | Daikuzono ........................... 606/16 X |
| 5,254,114 | 10/1993 | Reed, Jr. et al. ........................ 606/15 |
| 5,257,991 | 11/1993 | Fletcher et al. ........................... 606/17 |
| 5,269,777 | 12/1993 | Doiron et al. . |
| 5,290,275 | 3/1994 | Kittrell et al. . |
| 5,292,320 | 3/1994 | Brown et al. . |
| 5,300,063 | 4/1994 | Tano et al. . |
| 5,330,465 | 7/1994 | Doiron et al. . |
| 5,343,543 | 8/1994 | Novak, Jr. et al. . |
| 5,354,294 | 10/1994 | Chou ................................... 606/17 X |
| 5,401,270 | 3/1995 | Muller et al. . |

*Primary Examiner*—Angela D. Sykes
*Assistant Examiner*—Michael Peffley
*Attorney, Agent, or Firm*—H. Gordon Shields

[57] ABSTRACT

Side fire laser catheter apparatus includes a fiberoptic element having a bevelled tip fused to a cap. A secondary reflector may be disposed adjacent to the fiberoptic element as fused to the cap for reflecting any axial transmission outwardly through the cap. A lensed flat may be provided on the cap through which the laser beam is reflected to control the scattering of the light energy from the laser.

16 Claims, 2 Drawing Sheets

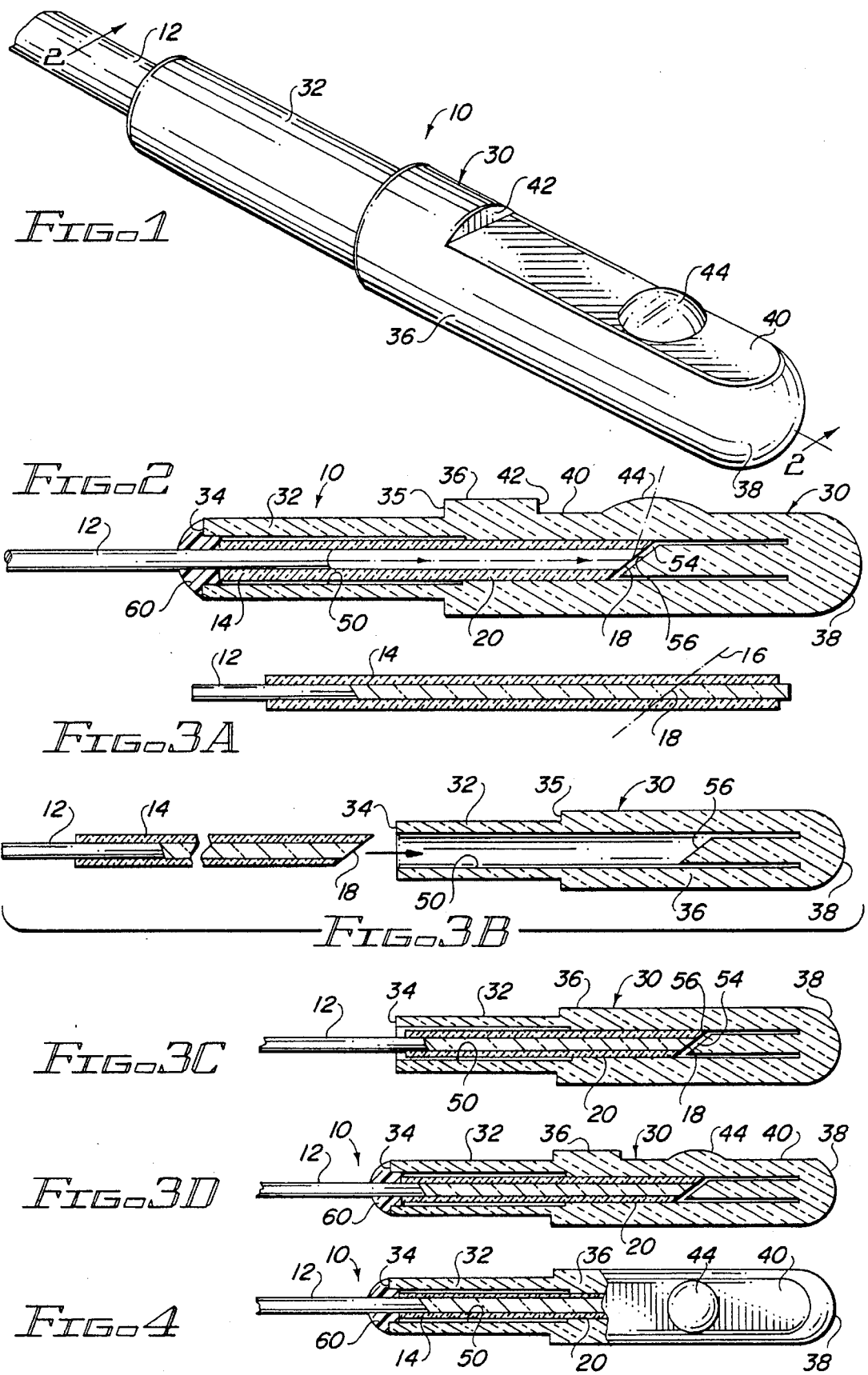

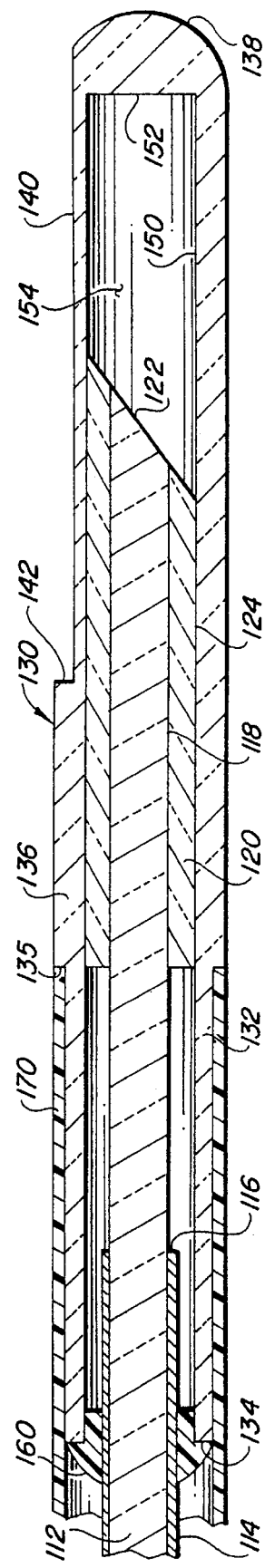
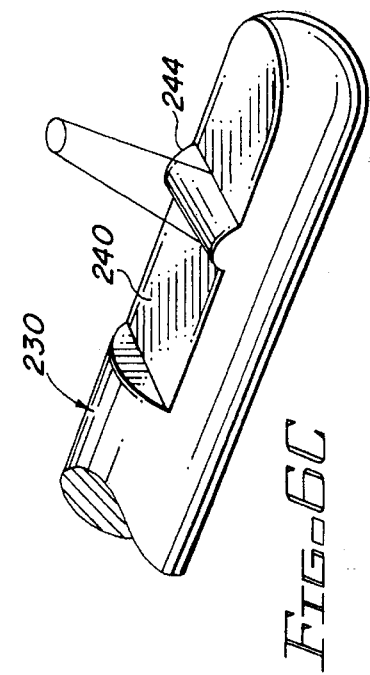
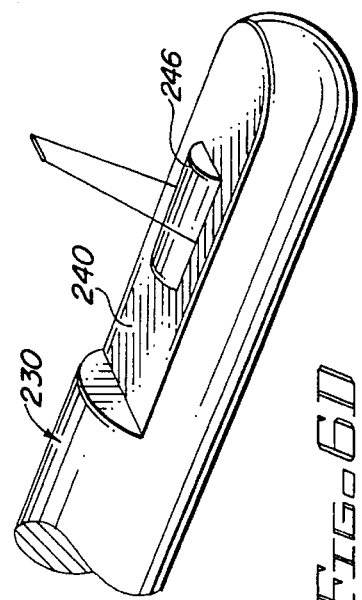
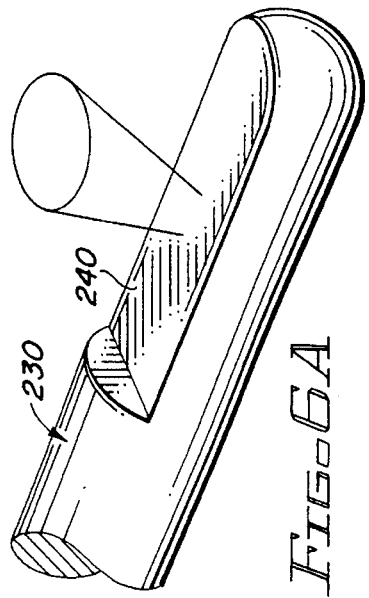
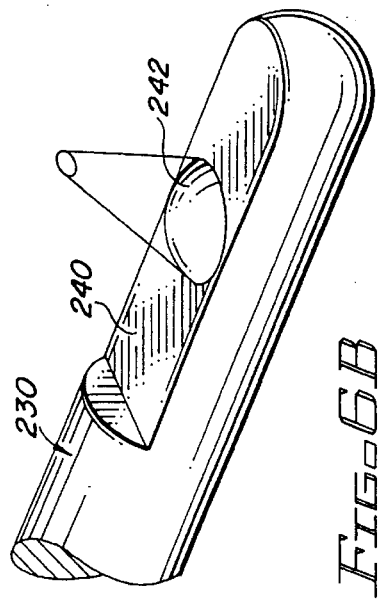

SIDE FIRE LASER CATHETER METHOD AND APPARATUS

BACKGROUND OF THE INVENTION

1. Field of the Invention

This invention relates to side fire laser fiberoptic catheter apparatus, and more particularly, to side fire laser fiberoptic catheter apparatus in which elements are fused together and in which laser output is controlled by a lensed flat or a configured lens on the catheter cap.

2. Description of the Prior Art

Side fire laser catheter elements using fiberoptics are in contemporary usage in disectomy, laparoscopy, arthroscopy, benign prostate hyperplasia, angioplasty, and other related surgical procedures.

The side fire laser catheter elements include a fiberoptic element disposed within a cap. The fiberoptic element has a tip cut and highly polished at a slant angle and disposed against or adjacent to a mating secondary reflector within the cap, separated only by a small air gap. When the laser is fired, the laser output beam is reflected primarily by total internal reflection due to the difference in refractive indicies of the fiber and the air in the gap, and the angle of the cut and polished fiber. Any radiation which escapes this reflection, axially, is reflected from a secondary reflector outwardly through the side of the catheter. Since the fiber and catheter cap are cylindrical, there are cylindrical distortions in the output of the fiber. Moreover, the tip of the fiberoptic typically includes rough edges and chips and scratches on the facet which contribute to the scattering of the laser output.

In the process of fabricating the cap, silica vapor is formed, and the vapor is deposited on the inside wall of the cap, causing adsorption and reflection of some portion of laser energy. The apparatus of the prior art is difficult to manufacture, and there is typically about a 60 percent rejection rate in the manufacturing process. Moreover, in the 40 percent of the side fire laser fiberoptic catheter apparatus that is not rejected, there is typically a substantial lack of control in the output of the laser due to the problems referred to above. This is undesirable because backscattered radiation & axial transmission can cause damage to healthy tissues.

In addition, the substantial portion of scattered energy, typically about 15%, contributes to heating of the assembly during operation. This heating may result in adhesion of tissue to the cap. Carbonization (burning) of the tissue results in further energy absorption, more heating, tissue adhesion, burning, and, ultimately, failure of the cap due to pitting in the silica.

The apparatus of the present invention overcomes the problems of the prior art, as discussed above, including the rejection rate, by sleeving the fiberoptic element with a fused silica cylinder prior to forming the chisel tip or facet and by fusing the fiberoptic element to the cap to form a single element, and by providing a lens or lensed flat on the cap aligned with the fiber facet, and secondary reflector if one is desired, for the control of the laser energy output. A secondary reflector may also be used, as when the output angle is less than about one hundred degrees or so. A lens formed on the cap flat may be convex, or cylindrical, depending upon the output shape desired.

It has been found that the apparatus of the present invention has an efficiency, as defined by the percent of injected power exiting through the desired solid angle, of greater than ninety nine percent, as compared to between about seventy and eighty five percent of the prior art.

SUMMARY OF THE INVENTION

The invention described and claimed herein comprises a side fire laser fiberoptic catheter apparatus utilizing an overclad or sleeved fiberoptic element, cut and polished to a desired critical angle for total internal reflection as defined by Snell's Law and a cap fused to the output end of the fiberoptic element. The fusing of the sleeved fiberoptic element to the cap provides a single element through which the laser output is reflected. A lensed flat on the cap adjacent to the reflective surface of the cap and the fiberoptic element provides the desired control of the output of the fiber. This results in an output beam which is reproducible and controlled. Moreover, the process involved in the manufacture of the side fire fiber laser catheter apparatus substantially eliminates rejected elements in the manufacturing process, which greatly increases both the average output of the catheter apparatus and the ultimate success of the catheter apparatus, and substantially decreases the cost involved in the manufacturing process.

Among the objects of the present invention are the following:

To provide new and useful side fire laser fiberoptic catheter apparatus;

To provide new and useful side fire laser catheter apparatus in which a sleeved fiberoptic element is fused to a catheter cap;

To provide new and useful method of making a side fired laser fiberoptic catheter apparatus;

To provide new and useful side fire laser fiber apparatus having a lens for controlling the output of the fiber;

To provide new and useful side fire laser catheter apparatus having a flat window on a cap; and To provide a new and useful method of making a fiberoptic element fused to a sleeve and a cap for a side fire laser catheter.

BRIEF DESCRIPTION OF THE DRAWING

FIG. 1 is a perspective view of the apparatus of the present invention.

FIG. 2 is a view in partial section taken generally along line 2—2 of FIG. 1.

FIG. 3A is a view in partial section illustrating the first step in making the apparatus of the present invention.

FIG. 3B is a side view in partial section illustrating the second step in making the apparatus of the present invention, sequentially following FIG. 3A.

FIG. 3C is a view in partial section illustrating the making of the apparatus of the present invention, sequentially following FIG. 3B.

FIG. 3D is a view in partial section illustrating the making of the apparatus of the present invention, sequentially following FIG. 3C.

FIG. 4 is a top view of the apparatus of the present invention with a portion shown in partial section.

FIG. 5 is a side view of an alternate embodiment of the present invention.

FIGS. 6A–6D comprise perspective views illustrating different lens configurations and the related output configurations of the apparatus of the present invention.

DESCRIPTION OF THE PREFERRED EMBODIMENT

FIG. 1 comprises a perspective view of a side fire fiber catheter apparatus 10 embodying the present invention. FIG. 2 comprises a view in partial section of the side fire catheter apparatus 10 of FIG. 1 taken generally along line 2—2 of FIG. 1. FIGS. 3A, 3B, 3C, and 3D comprise side views in partial section illustrating the fabrication of the apparatus 10. For the following discussion, reference will be primarily made to FIGS. 1, 2, and 3A–3D.

The side fire catheter apparatus 10 includes an optical fiber, or fiberoptic element, 12 disposed in a sleeve 14, and the optical fiber 12 and sleeve 14 are disposed in a cap 30. Laser energy in the form of a beam is transmitted in the fiberoptic element.

The cap 30 comprises a quartz element which is of a generally cylindrical configuration. The cap 30 includes a cylindrical rear portion 32 and a cylindrical front portion 36. The cylindrical rear portion 32 includes a rear end face 34, and the front cylindrical portion 36 includes a rounded front end 38. There is a step 35 between the cylindrical rear end portion 32 and the front portion 36. The diameter of the front portion 36 is greater than that of the rear portion 32. The step 35 accordingly comprises an outwardly extending shoulder between the lesser diameter rear portion 32 and the greater diameter front portion 36.

The cap 32 includes a top flat 40 which extends rearwardly from the front end 38 to a shoulder 42. The shoulder 42 comprises a transition between the circular configuration of the cylindrical portion 36 and the flat 40. A lens 44 extends upwardly on the flat 40.

Within the cap 30 is a bore 50. The bore 50 extends coaxially through both the cylindrical rear portion 32 and the cylindrical front portion 36. Within the bore 50, and disposed adjacent to the lens 44, is an angled face 56. The angled face 56 comprises a secondary reflective surface and, for all practical purposes, comprises the front end face of the bore 50.

FIG. 3A illustrates the optical fiber 12, which is preferably a buffered optical fiber, disposed in the sleeve 14. The buffered optical fiber and the sleeve are appropriately fused together. When the two elements have been fused together, a cut line 16 is made through both of them. The angle of the cut line 16 is the same as the cut line angle on the face 56 of the cap 30. The cut line 16 then results in an angled reflective face 18, at or lower than than the calculated critical angle, through the fused optical fiber 12 and sleeve 14. The angles are determined by Snell's Law, or the phenomenon of total internal reflection. In the manufacturing process, the angled reflective face 18 is appropriately polished to a high degree.

The reflective face 18 reflects laser energy in the form of a beam transmitted in the optical fiber 12. In the embodiment of the apparatus 10, the reflective face 18 comprises a primary reflective surface. The secondary reflective surface 56 has been discussed above.

The outer diameter of the fused optical fiber 12 and sleeve 14 is substantially the same as the inner diameter of the bore 50. In the manufacturing process, as indicated in FIG. 3B, the fiber 12 and sleeve 14, as fused together, with the now highly polished angled reflective face 18 disposed thereon, is inserted into the bore 50. This is shown in FIG. 3B. The reflective face 18 is disposed adjacent to the angled face 56 in the cap 30 and adjacent to and appropriately aligned with the flat 40 and the lens 44. The two faces 18 and 56 are disposed generally parallel to each other, and spaced apart a slight distance by a space 54. This is shown in FIGS. 2 and 3C.

When the optical fiber 12 and sleeve 14 are appropriately located within the cap 30, the angled reflective face 18 is appropriately located or aligned beneath the lens 44. Or, phrased in the opposite manner, the lens 44 is appropriately located or aligned above the angled faces, which comprise reflective surfaces 18 and 56. With the reflective surfaces 18 and 56 cut at an angle of about thirty nine degrees above the horizontal, the laser output energy will be angled outwardly generally as indicated by the dash dot line in FIG. 2, which angle is less than perpendicular or normal to the longitudinal axis of the bore 50.

After the fiber 12 and sleeve 14 have been located within the cap 30, the cap 30 is appropriately fused to the outside of the sleeve 14. Thus, the fiber 12, the sleeve 14, and the cap 30 are all fused together to comprise an integral element within the bore 50 of the cap 30.

In the manufacturing process, as indicated in FIGS. 3C and 3D, the optical fiber 12, sleeve 14, and cap 30 are fused together before the flat 40 and the lens 44 are formed on the front portion 36 of the cap 30. In FIG. 3C, there is shown a fused area or interface 20 between the outside of the sleeve 14 and the bore 50 of the cap 30 to secure the fiber 12, sleeve 14, and cap 30 together. Then, in FIG. 3D, the flat 40 is shown configured, with the convex lens 44 extending upwardly therefrom.

FIG. 4 comprises a top view of the assembled apparatus 10, with a portion broken away to show, in partial section, the fused area 20 of the cap 30 and the sleeve 14, with the optical fiber 12 in turn disposed within and secured thereto by fusing.

After the cap 30, the sleeve 14, and the optical fiber 12 have been secured together, the bore 50 about the optical fiber 12 is sealed by an end seal 60 of epoxy cement. The end seal 60 functions as strain relief for the fused elements.

As indicated above, the sleeve is fused to the optical fiber, and the cap is in turn fused to the sleeve. The optical fiber 12 is typically of a fused silica core with a cladding of fluorine doped fused silica. The sleeve 14 is also fused silica, as is the cap 30. Accordingly, when the three elements are fused together, they comprise a unitary element through which the laser beam passes with minimal, if any at all, scattering or distortion of the laser beam. Thus, instead of having a multiplicity of separate surfaces, each of which comprises a reflective surface to the laser beam, the fused elements comprise a single, unitary element to the laser beam.

FIG. 5 is a view in partial section through an alternate embodiment of the apparatus 10 of FIGS. 1–4. The embodiment of FIG. 5 comprises a side fire fiber catheter apparatus 110.

The side fire fiber catheter apparatus 110 includes an optical fiber 112, with a buffered outer portion 114, extending into a bore 150 of a cap 130. The buffered outer portion 114 of the fiber 112 extends only part way into the bore 150 and terminates at a shoulder 116. The bare optical fiber 112 then continues inwardly.

At the front portion of the optical fiber 112 is a sleeve 120. The optical fiber 112 is fused to the sleeve 120 at an area indicated by reference numeral 118. This is substantially identical to the fused area of the optical fiber 12 and its sleeve 14 of the apparatus 10 of FIGS. 1–4.

The front of the fiber 112 and its sleeve 120 is cut at an angle to comprise a front face 122. The front face 122 is polished, as discussed above, to comprise a reflective surface for a laser beam.

The fiber 112 and sleeve 120 are also fused to the cap 130 in a fused area indicated by reference numeral 124. This is substantially the same as or corresponds to, the fused area 20 of the apparatus 10, discussed above.

The cap 130 also includes a rear cylindrical portion 132 which terminates in a rear end face 134. The cap 132 also includes a front cylindrical portion 136. An outwardly extending shoulder 135 defines the area between the rear, lesser diameter portion 132 and the front, greater diameter, portion 136.

The cap 130 further includes a top flat 140 which extends rearwardly from a rounded front end 138 and terminates in a shoulder 142. Again, the top flat 140 is comparable to the top flat 40 of the apparatus 10.

In the manufacturing process of forming the apparatus 110, the top flat 140 is oriented or aligned relative to the front face 122 so that the laser beam energy is reflected directly through the top flat 140, generally perpendicular thereto.

It will be noted that there is no lens on the flat 140. As indicated above, a lens may or may not be needed, depending on the desired configuration of the laser beam. This will be discussed below in more detail.

The bore 150 terminates in a front end 152. In the manufacturing process, a chamber 154 becomes essentially a hermetically sealed vacuum chamber when the fiber 112 and the sleeve 120 are fused in the bore 150 to the cap 130. The chamber 154 is defined within the bore 150 between the face 122 and the end 152.

To seal the bore 150, an end cap 160 is disposed at the face 134 of the end cap 130 and about the buffered optical fiber 112/114. The end seal 160 is an epoxy which provides the strain relief for the essentially quartz elements, the buffered optical fiber 112/114, and the cap 130.

The fiberoptic element or optical fiber 112, with its buffered outer portion 114, the sleeve 120, and the cap 130, are all made of fused silica, as discussed above.

For surgical purposes, a heat shrink outer sleeve 170 is disposed on the rear portion 132 of the cap 130 and against the shoulder 135. The outer sleeve 170 extends rearwardly from the cap 130 and along the buffered optical fiber 112/114, as desired.

In addition to the lens 44 as discussed with the apparatus 10, there are other types of lenses which may be used, as desired, for different surgical applications of the side fire fiber catheter apparatus of the present invention. Different lenses are illustrated in FIGS. 6A, 6B, 6C, and 6D. Each of the FIGS. 6A–6D comprise perspective views of the front flat portion of a cap 230, with different configurations of lenses thereon for appropriately focusing laser energy.

In FIG. 6A, an end cap 230 includes a top front flat portion 240. This is as shown in FIG. 5, in which the top flat 140 is shown as planar. Without a specific lens, the output of the laser provides a diverging beam having a generally circular crossectional configuration.

In FIG. 6B, a convex lens 242 extends upwardly from a flat 240. This is similar to the lens 44 of the apparatus 10. The output of the laser beam from the convex lens 242 comprises a beam having a crossectional configuration of a converging spot.

In FIG. 6C, there is a cylindrical lens 244 which extends upwardly from the flat 240. The cylindrical lens 244 is generally perpendicular to the longitudinal access of the cap 230, and accordingly generally perpendicular to the optical fiber disposed within the cap 230. The output of a laser beam from the cylinder 244 has a crossectional configuration of a converging ellipse.

In FIG. 6D, a lens 246 having a cylindrical configuration extending generally parallel to the longitudinal axis of the cap 230. The output through the parallel cylindrical lens 246 has a crossectional configuration of a converging line.

With regard to FIG. 6D, it will be noted that the configuration of the top or upper portion of the cap 30 as shown in FIGS. 3B and 3C comprises a convex lens parallel to and above the longitudinal axis of the cap. Accordingly, if a line output parallel to the longitudinal axis of the cap is desired, the flat 40, with the lens 246, need not be configured on the cap 30. In other words, the cylindrical wall 36 of the cap 30 may provide a satisfactory lens by itself.

It will also be noted that the apparatus 130 of FIG. 5 does not include a secondary reflector, as does the apparatus 10 of FIGS. 1–4. The primary need for a secondary reflector is found when a facet angle is above or greater than the critical angle for total internal reflection, as defined by Snell's Law, for the wavelength and refractive indices in question.

It will be understood that any desirable lens configuration may be formed on the flat to provide the desired output beam reflected from the front end faces of the optical fibers in the various embodiments of the apparatus of the present invention.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What is claimed is:

1. Side fire laser fiberoptic catheter apparatus comprising in combination:

a fiberoptic element through which laser energy is transmitted;

a sleeve disposed about and fused to the fiberoptic element;

a reflective face on the fused fiberoptic element and sleeve for reflecting the laser energy;

a cap, including a bore for receiving the fused fiberoptic element and sleeve, and in which the fused fiberoptic element and sleeve are fused to the cap; and a flat on the cap, and a lens on the flat through which the reflected laser energy passes.

2. The apparatus of claim 1 in which the cap further includes a reflective surface generally parallel to the reflective face on the fiberoptic element for reflecting laser energy.

3. The apparatus of claim 1 in which the lens is convex.

4. The apparatus of claim 1 in which the lens comprises a cylinder.

5. The apparatus of claim 4 in which the bore in the cap has a longitudinal axis and the cylinder is generally perpendicular to the longitudinal axis.

6. The apparatus of claim 4 in which the bore in the cap has a longitudinal axis and the cylinder is generally parallel to the longitudinal axis.

7. The apparatus of claim 1 in which the bore in the cap includes a front end spaced apart from the reflective face, and a chamber is defined in the bore between the reflective face and the front end.

8. Side fire laser catheter apparatus comprising in combination:
- a generally cylindrical cap;
- a bore extending into the cap;
- a fiberoptic element for transmitting laser energy;
- a sleeve fused to the fiberoptic element, and the fused sleeve and fiberoptic element are disposed in the bore and fused in the bore to the cap;
- a reflective face on the fused fiberoptic element and sleeve for reflecting the laser energy outwardly from the cap;
- a flat on the cap aligned with the reflective face; and
- a lens on the flat through which the laser energy is transmitted.

9. The apparatus of claim 8 in which the reflective face comprises a polished, beveled surface extending through the sleeve and fiberoptic element.

10. A method of making a side fire laser catheter comprising in combination the steps of:
- providing a fiberoptic element;
- providing a sleeve for the fiberoptic element;
- fusing the fiberoptic element to the sleeve;
- cutting the fused fiberoptic element and sleeve at an angle to provide a reflective face for reflecting laser energy;
- polishing the reflective face;
- providing a cap having a bore;
- disposing the fused fiberoptic element and sleeve and polished reflective face in the bore;
- fusing the sleeve in the bore to the cap to provide a unitary fiberoptic element, sleeve, and cap;
- providing a planar flat on the cap appropriately aligned with the reflective face; and
- providing a lens on the planar flat through which laser energy is focussed.

11. The method of claim 10 in which the step of providing a lens on the planar flat includes the step of providing a convex lens.

12. The method of claim 10 in which the step of providing a lens on the planar flat includes the step of providing a cylindrical lens.

13. The method of claim 10 which further includes the step of providing a secondary reflective face in the bore.

14. The method of claim 13 which further includes the step of placing the reflective face of the fused fiberoptic and sleeve parallel and adjacent to the secondary reflective face.

15. A device for directing light from a light source such as a laser, comprising
- an elongated optical fiber having a longitudinal axis for directing light received at its proximal end to its distal end;
- a transparent sleeve fused to said optical fiber in at least a distal portion thereof, the distal ends of said fused sleeve and fiber being cut to form a beveled end, and which beveled end is polished to provide a reflective surface, and
- the light transmitted through the fiber being reflected internally from the end of the fiber through a portion of said sleeve;
- a transparent cap fused to said sleeve in at least a region in which the sleeve and fiber are fused together and enclosing the distal ends of the fiber and sleeve, whereby the light reflected from the beveled distal surface of said fiber exits through the fused region of the sleeve and cap without passing through any gas-solid interface; and
- a lens on the cap for directing light reflected from the reflective surface of the beveled end.

16. The device of claim 15 in which the lens on the cap is convex.

* * * * *